(12) United States Patent
Karolchyk

(10) Patent No.: US 11,660,284 B2
(45) Date of Patent: May 30, 2023

(54) SELF-EMULSIFYING ANHYDROUS INTRADERMAL DEPOT GEL

(71) Applicant: MEDPHARM HOLDINGS, LLC, Denver, CO (US)

(72) Inventor: Scott Karolchyk, Denver, CO (US)

(73) Assignee: MEDPHARM HOLDINGS, LLC, Denver, CO (US)

( * ) Notice: Subject to any disclaimer, the term of this patent is extended or adjusted under 35 U.S.C. 154(b) by 244 days.

(21) Appl. No.: 17/069,519

(22) Filed: Oct. 13, 2020

(65) Prior Publication Data
US 2021/0106554 A1    Apr. 15, 2021

Related U.S. Application Data

(60) Provisional application No. 62/914,659, filed on Oct. 14, 2019.

(51) Int. Cl.
| | |
|---|---|
| *A61K 31/352* | (2006.01) |
| *A61K 9/00* | (2006.01) |
| *A61K 47/10* | (2017.01) |
| *A61K 47/42* | (2017.01) |
| *A61K 47/38* | (2006.01) |
| *A61K 47/18* | (2017.01) |
| *A61K 31/05* | (2006.01) |
| *A61K 47/12* | (2006.01) |

(52) U.S. Cl.
CPC .......... *A61K 31/352* (2013.01); *A61K 9/0024* (2013.01); *A61K 31/05* (2013.01); *A61K 47/10* (2013.01); *A61K 47/12* (2013.01); *A61K 47/183* (2013.01); *A61K 47/38* (2013.01); *A61K 47/42* (2013.01)

(58) Field of Classification Search
CPC .................................................. A61K 31/352
See application file for complete search history.

(56) References Cited

U.S. PATENT DOCUMENTS

| | | | |
|---|---|---|---|
| 2020/0197358 A1* | 6/2020 | Eades | A61K 47/10 |
| 2020/0222362 A1* | 7/2020 | Kaur | A61K 47/10 |

OTHER PUBLICATIONS

Wadhwa, Brazilian Journal of Pharmaceutical Sciences, vol. 47, n. 3, 2011.*
Truong AAPS PharmSciTech, vol. 17, No. 2, Apr. 2016, 466-473.*

* cited by examiner

*Primary Examiner* — Nizal S Chandrakumar
(74) *Attorney, Agent, or Firm* — Nyemaster Goode P.C.

(57) ABSTRACT

The present invention relates to compositions and methods to solubilize poorly water-soluble medicaments using a self-emulsifying, anhydrous gel (SEAG), which then forms an intradermal depot when absorbed. The gel preferably comprises a mixture of propylene glycol, glycerin, ethoxy diglycol, hydroxypropylcellulose, butylated hydroxytoluene, caprylic acid triglyceride and edetate disodium, and may further include an oral-based, bioadhesive paste, which allows the gel to adhere mucosally. The SEAG may further contain a solubilizer such as Kolliphor HS15.

5 Claims, No Drawings

SELF-EMULSIFYING ANHYDROUS INTRADERMAL DEPOT GEL

CROSS-REFERENCE TO RELATED APPLICATIONS

This application claims the benefit of priority to U.S. Provisional Patent Application No. 62/914,659, filed Oct. 14, 2019, entitled "SELF-EMULSIFYING ANHYDROUS INTRADERMAL DEPOT GEL," is hereby incorporated by reference in its entirety.

BACKGROUND OF THE INVENTION

The therapeutic efficacy of a drug depends upon its bioavailability, which is directly correlated to its solubility. A drug must be in solution form for it to be absorbed regardless of the route of administration. Many drugs, both in development and on the market, are poorly soluble in aqueous media, which can lead to poor bioavailability and frequently results in variable dissolution rates. To achieve the desired drug concentration in systemic circulation to elicit a pharmacological response, solubility is paramount.

Even though tetrahydrocannabinol (THC) and cannabidiol (CBD) possess a wide range of activities, including anti-inflammation and analgesia, the administration of these components has been hampered by their extreme water insolubility and poor bioavailability. Various strategies have been used to overcome problems associated with oral and topical absorption and bioavailability of poorly soluble drugs, such as particle size reduction, complexation with cyclodextrins, salt formation, solid dispersions, use of surfactants, nanoparticles, nanocarriers, nanoemulsions, prodrug formation, etc.

There is therefore a need in the industry for an effective means of solubilizing THC, CBD and other water-insoluble drugs.

To overcome these problems, delivery of these cannabinoids using a novel self-emulsifying anhydrous gel (SEAG) will likely yield more promising clinical applications in the near future.

SUMMARY OF THE INVENTION

A self-emulsifying, anhydrous gel (SEAG), which forms an intradermal depot of the active ingredients after being absorbed, is provided which has use as carrier for topical delivery of poorly water-soluble medicaments including cannabis, terpenes and minor cannabinoids, intra-orally and externally. In one embodiment, the SEAG comprises a mixture of propylene glycol, glycerin, ethoxy diglycol, hydroxypropylcellulose, butylated hydroxytoluene, caprylic acid triglyceride and edetate disodium. This combination allows an intra-dermal depot of the actives to occur, providing an increased duration of action. The invention also comprises a combination of the carrier, with an oral-based, bioadhesive paste, which allows the gel to adhere mucosally when used orally for use, for example, in conjuction with a stent or other dental appliance. In another embodiment of the invention, the SEAG further includes a solubilizer/emulsifier, such as Kollipher HS15 or lecithin.

DETAILED DESCRIPTION OF THE PREFERRED EMBODIMENT

The invention relates to the use of a self-emulsifying anhydrous gel (SEAG) for use in solubilizing THC, CBD, all terpenes, flavonoids, minor cannabinoids and other water-insoluble drugs.

SEAG is a hydrophilic solvent-based, anhydrous drug delivery system, utilizing ethoxy diglycol, which presents the cannabinoids in a solubilized state in a solubilized dispersion. It is a gel containing solid or liquid surfactants, one or more hydrophilic solvents which have the unique ability to form fine oil-in-water emulsions when in contact with aqueous media, such as saliva. SEAG is different than SNEDDS, which is a self-nanoemulsifying drug delivery system, which contains water or can be diluted in water. In one embodiment of the invention, the SEAG further includes a solubilizer/emulsifier such as Kolliphor HS15 or lecithin.

The innovation of the present invention stems from ethoxy diglycol (EG) and its ratio of propylene glycol (PG)(or other solvent) to glycerin (or other co-solvent), and the use of different ratios depending upon the depth of skin penetration needed. More particularly, the ratios of EG:PG determine the depth of penetration, whereby a higher ratio of EG provides shallower penetration, which is advantageous in targeting nerve endings in the intra-dermal layer.

The inventors have also found that the EG concentration affects drug retention in the skin to form a cutaneous depot. In this regard, EG causes swelling of the intracellular space, also causing swelling of intercellular lipids, without alteration of the multiple bilayer structure. These swollen lipids then retain drugs, especially lipophilic compounds. This results in increased skin retention and a simultaneous decrease in transdermal permeation.

Ethoxy diglycol (EG), also known as diethylene glycol monoethyl ether, carbitol, and transcutoldiethylene glycol monoethyl ether, is a liquid which has a long history of use in cosmetic and over-the-counter topically applied products. EG has been used in formulations as a co-surfactant and a penetration enhancer, and has been frequently utilized in topical formulations (dermal drug delivery systems), transdermal delivery systems, and ocular and also intranasal delivery systems. It is also used as an ingredient in nanoemulsions, sunless tanning products, and in a wide range of hair-coloring products which are rinse-off products. To date, however, EG has not been used in an anhydrous gel form that self-emulsifies active medications such as cannabinoids.

In one aspect, the invention comprises a pharmaceutical gel for oral and topical application of medicaments, consisting of a SEAG comprising at least 1% by weight ethoxy diglycol (EG), at least 1% by weight PG (or other solvent), and at least 1% by weight glycerin (or other other co-solvent). In one embodiment of the invention, the SEAG further includes at least 1% by weight of a solubilizer, such as Kolliphor HS15 or lecithin. In one embodiment of the invention, the pharmaceutical composition preferably includes between about 1-85% by weight EG, with about 40-80% by weight being preferred, between 1-20% by weight Kolliphor HS15, with about 3-10% by weight being preferred, between about 1-40% PG, with about 10-30% by weight being preferred, and about 1-40% by weight glycerin, with about 10-30% being preferred.

The solvent in the composition may be PG or other solvent including, but not limited to, vegetable glycerin, and/or propanediol derivatives, or other natural glycols that enhance hydration and absorption through the skin. The co-solvent may be glycerin or other co-solvent including, but not limited to, propylene glycol and/or monoglycerides. However, the solvent and co-solvent cannot both be PG.

Polyoxyethlene-660-12-hydroxystearate (Kolliphor HS15) is a graft polymer frequently used as a stabilizer in topical formulations (dermal drug delivery systems), transdermal delivery systems, parenteral, ocular and intranasal delivery systems. It provides a steric stabilization mechanism and is a great solubilizer. It is also used as a novel ingredient in emulsions, sunless tanning products, and in a wide range or hair-coloring products. It is a non-ionic surfactant that has not previously been used in SENE form to emulsify active medications such as cannabinoids. It keeps the acceptable nanoemulsion properties intact, protecting the emulsion from harsh conditions such as high temperature, shear stresses and ionic medication loads. Chemical names for Kolliphor HS15 include Solutol HS15, polyoxyl 15 hydroxystearate, and macrogol 660 hydroxystearate. Other acceptable solubilizers/non-ionic surfactants suitable for this purpose include lecithins, polyglycerol alkyl ethers, glucosyl dialkyl ethers, crownethers, ester-linked surfactants, polyoxyethylene alkyl ethers, Brij, Spans (sorbitan esters) and Tweens (polysorbates). If included, the composition of the invention should include at least 0.01% by weight solubilizer, with a range of about 0.05-2.0% being preferred.

The pharmaceutical gel preferably also includes a thickening agent that may include, but is not limited to, hydroxypropylcellulose (HPC), hydroxyl ethyl cellulose (HPC) and derivatives thereof, hydroxyl methyl cellulose (HMC) and derivatives thereof, carboxycellulose, carboxymethylcellulose, quaternized cellulose, gelatin, agar, chitosan, carrageenan, arrowroot, and guar gum. If included, the composition of the invention should include at least 0.1% by weight thickening agent, with a range of about 0.1-10% by weight being preferred.

In another embodiment, the invention includes an antioxidant that may include, but is not limited to, butylated hydroxytoluene, ascorbic acid and its salts, vitamin E, sodium metabisulfite, polyphenol, ascorbyl palmitate, propyl gallate, butylated hydroxyanisole (BHA), and cysteine. If included, the composition of the invention should include at least 0.01% antioxidant, with a range of about 0.01-0.5% by weight being preferred.

In another embodiment, the invention includes a chelation agent that may include, but is not limited to edetate disodium (EDTA), EDTA sodium calcium, triethylenetetramine, tetraacetylethylenediamine, PMDTA, ED TA tetrasodium, and EDTA calcium. If included, the composition of the invention should include at least 0.01% by weight chelation agent, with a range of about 0.1-1.0% by weight being preferred.

In another embodiment, the invention includes an emulsion-forming carrier that may include, but is not limited to, caprylic acid triglyceride, vegetable oils, coconut oils, medium-chain triglycerides (MCT) oils, long-chain triglycerides (LCT) oils, avocado oil, walnut oil, flax oil, and hemp oil. If included, the composition of the invention should include at least 0.1% by weight caprylic acid triglyceride, with about 0.1-10% by weight being preferred.

In a preferred embodiment, the gel formulation includes about 58% by weight EG, about 20% by weight PG, and about 20% by weight glycerin, about 1% by weight (HPC), about 0.05% by weight BHT, about 0.05% by weight edetate disodium, and about 5% caprylic acid triglyceride (if warranted) being preferred.

In another aspect, the invention comprises a bioadhesive, intra-oral paste, which includes the addition of gelling agents, a stabilizer, a thickener, and a plasticized base. The bioadhesive paste allows the gel to adhere mucosally when used orally for use, for example, in conjunction with a stent or other dental appliance.

The gelling agent may include, but is not limited to, gelatin, agar, chitosan, carrageenan, sodium carboxymethylcellulose, arrowroot, and guar gum. The gelling agents should be used in an amount of at least 0.1% by weight, with about 0.1-5.0% by weight being preferred and about 1.0% by weight being most preferred. The stabilizer may include, but is not limited to, pectin and cornstarch. The stabilizer should be used in an amount of at least 0.1% by weight, with about 0.1-5.0% by weight being preferred, and about 1.0% by weight being most preferred. The thickeners may include, but is not limited to, xanthum gum, agar, arrowroot, cornstarch, guar gum, carrageenan, gum arabic, locust bean gum, and gum tragacanth. The thickener should be used in an amount of at least 0.1% by weight, with about 0.1-5.0% by weight being preferred, and about 1.0% by weight being most preferred. The plasticized base may include, but is not limited to, oleogels, structured mineral oil, hydrophilic petrolatum, unsaturated triglyceride oils, triacylglycerols, natural food waxes, fatty acid derivatives, direct and indirect dispersion. The plasticized base should be present in an amount of at least 10% by weight of the composition, with between about 10-85% by weight being preferred and about 50% by weight being most preferred. Finally, the intra-oral paste should include ethanol in an amount of at least 0.1% by weight, with about 0.1-10% by weight being preferred and about 1.0% by weight being most preferred.

The compositions of the invention may optionally include other ingredients, such as antioxidants, flavors, colors, vitamins, minerals, etc. so long as the other ingredients are compatible with the other ingredients of the formulation. The compositions may also be combined with a pharmaceutically acceptable carrier that may include one or more carriers or excipients, such as fillers, diluents, binders, lubricants, and disintegrants. Such ingredients and their relative amounts to be included are well known to persons skilled in the art.

According to at least one embodiment, the ingredients of the formulation may be combined by simply mixing at room temperature (25-30° C.) with or without agitation, followed by heating from about 60-100° C. then mixing until the composition is clear. The composition is then cooled prior to use. The ingredients of the invention can either be mixed sequentially or can be added all at once to achieve the unique composition of the invention. In preferred embodiments the ingredients are mixed with agitation to improve miscibility.

While the compositions are described specifically for use with CBD and THC, they may be used to solubilize and drug or medication that is insoluble or only partially soluble in water. The SEAGs of the invention should be combined with the drug in an amount necessary to solubilize the drug or medication to be solubilized. In general, the amount of drug to SEAG to will be from 0.1-50% by weight drug to SEAG.

The following examples are offered to illustrate but not limit the invention. Thus, it is presented with the understanding that various formulation modifications as well as method of delivery modifications may be made and still are within the spirit of the invention.

EXAMPLES

Preferred SEAG Gel Composition

| | |
|---|---|
| Propylene Glycol | 1-40 gm |
| Ethoxy diglycol | 1-85 gm |
| Kolliphore HS15 | 1-20 gm |
| Glycerin | 1-40 gm |
| Hydroxypropylcellulose | 0.1-10 gm |
| Butylated Hydroxytoluene | 0.01-0.5 gm |

|  |  |
| --- | --- |
| Edetate Disodium | 0.01-1 gm |
| Caprylic acid triglyceride | 0-10 gm |

Procedure:
1. Combine HPC, Kolliphor HS15 and EG, mix for 2 minutes
2. Combine all ingredients and mix well
3. Heat to 70 C and spin until mix is clear
4. Allow to cool to room temperature In a second aspect, a bioadhesive, intra-oral paste is added to the gel, comprising a mixture of the following:

|  |  |
| --- | --- |
| Gelatin | 0.1-5 gm |
| Pectin | 0.1-5 gm |
| Sodium carboxymethylcellulose | 0.1-5 gm |
| Plasticized base | 10-85 gm |
| Water, preserved | 10-85 gm |
| Ethanol, 95% | 0.1-10 gm |
| Xanthum gum | 0.1-5 gm |

Procedure:
1. Add all powders to the ethanol
2. Add water, boiling, all at once
3. Stir well, allow to cool, covered
4. Mill mixture into plastibase, mix well It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The foregoing description has been presented for the purposes of illustration and description. It is not intended to be an exhaustive list or limit the invention to the precise forms disclosed. It is contemplated that other alternative processes and methods obvious to those skilled in the art are considered included in the invention. The description is merely examples of embodiments. It is understood that any other modifications, substitutions, and/or additions may be made, which are within the intended spirit and scope of the disclosure. From the foregoing, it can be seen that the exemplary aspects of the disclosure accomplishes at least all of the intended objectives.

The invention claimed is:

1. A self-emulsifying, anhydrous gel (SEAG) intradermal gel consisting essentially of:
    40-80% by weight ethyoxy diglycol (EDG);
    10-30% by weight propylene glycol;
    10-30% by weight glycerin;
    3-10% by weight polyoxyethylene-660-12-hydroxystearate;
    hydroxypropylcellulose;
    butylated hydroxytoluene;
    caprylic acid triglyceride; and
    edetate disodium.

2. The self-emulsifying, anhydrous gel (SEAG) intradermal gel of claim 1 comprising:
    58% by weight ethyoxy diglycol (EDG);
    20% by weight propylene glycol (PG);
    20% by weight glycerin;
    1% by weight hydroxypropylcellulose (HPC);
    0.05% by weight butylated hydroxytoluene (BHT); and
    0.05% by weight edetate disodium.

3. The self-emulsifying, anhydrous (SEAG) intradermal gel of claim 2 further including 5% caprylic acid triglyceride.

4. A self-emulsifying, anhydrous gel (SEAG) intradermal gel comprising:
    1-40 gm of propylene glycol;
    1-85 gm of ethyoxy diglycol;
    1-20 gm of polyoxyethylene-660-12-hydroxystearate;
    1-40 gm of glycerin;
    0.1-10 gm of hydroxypropylcellulose;
    0.01-0.5 gm of butylated hydroxytoluene;
    0.01-1 gm of edetate disodium; and
    0-10 gm of caprylic acid triglyceride.

5. The SEAG of claim 4 further including:
    0.1-5 gm of gelatin;
    0.1-5 gm of pectin;
    0.1-5 gm of sodium carboxymethylcellulose;
    10-85 gm of plasticized base;
    0.1-10 gm of ethanol; and
    0.1-5 gm of xanthum gum.

\* \* \* \* \*